US012806075B2

(12) United States Patent
Marashi

(10) Patent No.: US 12,806,075 B2
(45) Date of Patent: Nov. 24, 2026

(54) OPHTHALMOLOGICAL TREATMENT AND MANUFACTURE APPARATUS

(71) Applicant: Ziemer Ophthalmic Systems AG, Port (CH)

(72) Inventor: Mohamad Omar Marashi, Aleppo (SY)

(73) Assignee: Ziemer Ophthalmic Systems AG, Port (CH)

(*) Notice: Subject to any disclaimer, the term of this patent is extended or adjusted under 35 U.S.C. 154(b) by 906 days.

(21) Appl. No.: 18/075,569

(22) Filed: Dec. 6, 2022

(65) Prior Publication Data

US 2023/0172754 A1 Jun. 8, 2023

(30) Foreign Application Priority Data

Dec. 6, 2021 (CH) ................................ 70655/2021

(51) Int. Cl.
*A61F 9/008* (2006.01)
*A61F 2/14* (2006.01)

(52) U.S. Cl.
CPC .............. *A61F 9/008* (2013.01); *A61F 2/142* (2013.01); *A61F 2009/00872* (2013.01)

(58) Field of Classification Search
CPC .. A61F 9/008; A61F 9/00802; A61F 9/00827; A61F 2/142; A61F 2009/00872; A61F 2009/00878

(Continued)

(56) References Cited

U.S. PATENT DOCUMENTS

| | | | |
|---|---|---|---|
| 9,849,037 | B2 | 12/2017 | Rathjen et al. |
| 2006/0100612 | A1 | 5/2006 | van der Heyd et al. |

(Continued)

FOREIGN PATENT DOCUMENTS

| | | | |
|---|---|---|---|
| EP | 2853247 | A1 | 4/2015 |
| IT | 201800009697 | A1 | 4/2020 |

(Continued)

OTHER PUBLICATIONS

Mar. 18, 2022—(CH) International Search Report—App 070655/2021.

*Primary Examiner* — Aaron F Roane
(74) *Attorney, Agent, or Firm* — Banner & Witcoff, Ltd.

(57) ABSTRACT

An ophthalmological treatment apparatus for resecting a patient cornea element form a patient cornea in posterior lamellar keratoplasty, an ophthalmological manufacture apparatus for manufacturing from a donor cornea a cornea implant, as well as corresponding manufacture and implantation methods are disclosed. The patient cornea cut pattern that is implemented in the patient cornea defines a patient cornea interlocking structure, the patient cornea interlocking structure being configured to interlock the patient cornea with a cornea implant after replacing the patient cornea element by the cornea implant. The corneal implant may have a corresponding cornea implant interlocking structure. The patient cornea interlocking structure and the cornea implant interlocking structure may be arranged at the posterior side of the patient cornea element and the cornea implant, respectively. The ophthalmological treatment apparatus and the ophthalmological manufacture apparatus may include in each case an ophthalmological laser device, in particular with a femtosecond laser source.

9 Claims, 4 Drawing Sheets

(58) Field of Classification Search
USPC .............................................................. 606/5
See application file for complete search history.

(56) References Cited

U.S. PATENT DOCUMENTS

| | | | | |
|---|---|---|---|---|
| 2008/0058777 | A1 | 3/2008 | Kurtz et al. | |
| 2008/0082086 | A1 | 4/2008 | Kurtz et al. | |
| 2008/0082088 | A1 | 4/2008 | Kurtz et al. | |
| 2019/0159934 | A1* | 5/2019 | Bischoff ............. | A61F 9/00802 |
| 2020/0146812 | A1* | 5/2020 | Klopotek ............ | A61F 9/00836 |
| 2021/0113375 | A1* | 4/2021 | Peyman .............. | A61F 9/00827 |
| 2022/0054316 | A1* | 2/2022 | Voorhees ............ | A61F 9/00827 |

FOREIGN PATENT DOCUMENTS

| | | | |
|---|---|---|---|
| WO | 2004017878 | A1 | 3/2004 |
| WO | 2008030699 | A2 | 3/2008 |

* cited by examiner

OPHTHALMOLOGICAL TREATMENT AND MANUFACTURE APPARATUS

CROSS-REFERENCE TO RELATED APPLICATION

The present application claims priority to and the benefit of Switzerland Patent Application 070655/2021 filed Dec. 6, 2021, which is incorporated by reference in its entirety herein.

TECHNICAL FIELD

The present disclosure relates to the field of ophthalmological surgery, in particular posterior lamellar keratoplasty. Specifically, it relates to ophthalmological treatment apparatus and ophthalmological manufacture apparatuses, as well related methods. The disclosure further relates to cornea implants.

BACKGROUND, PRIOR ART

In posterior lamellar keratoplasty, a pathological respectively defective patient cornea element of a patient cornea is resected and is replaced with a cornea implant which may be manufactured from a donor cornea. The patient cornea element and accordingly the cornea implant are adjacent to the anterior chamber. For resecting the patient cornea element as well as manufacturing the cornea implant a suited surgical, in particular ophthalmological, laser device.

SUMMARY OF DISCLOSURE

A number of apparatuses and procedures for posterior lamellar keratoplasty are generally known in the art, for example form US 2008/0082088 A1. The involved procedures, however, are generally highly complex and critical, with a substantive risk for damaging the patient's eye. This particularly concerns the removal of the resected patient cornea element as well as the insertion and positioning of the tissue implant. Further there is a general risk for the resected patient cornea element as well as the cornea implant to fall into the anterior chamber of the patient eye. Also, correct positioning of the cornea implant without undesired movement thereof subsequent to insertion is critical.

WO2008/030699A2 describes an approach where annular incisions and side cuts are impended in the donor as well as the patient cornea tissue to allow securing of the cornea implant. The resulting geometry, however, is complex and actually inserting and positioning the cornea implant difficult.

It is an overall advantage of the present disclosure to improve the state of the art regarding posterior lamellar keratoplasty. Favorably, at least some of the before-mentioned drawbacks of the prior art are reduced and favorably avoided.

In an aspect, the present disclosure concerns an ophthalmological treatment apparatus for resecting a patient cornea element form a patient cornea in posterior lamellar keratoplasty. The ophthalmological treatment apparatus includes a treatment laser device for implementing cornea cuts. The ophthalmological treatment apparatus further includes a computerized treatment control device in operative coupling with the treatment laser device, the treatment control device being designed to control the treatment laser device to implement a number of patient cornea cuts. The patient cornea cuts form, in combination, a patient cornea cut pattern. A geometry of the patient cornea element is defined by the patient cornea cut pattern.

The number of patient cornea cuts include a patient anterior lamellar cut. The patient anterior lamellar cut extends in the patient cornea at a patient anterior lamellar cut distance from a patient posterior cornea surface. The patient anterior lamellar cut defines a patient anterior cornea element surface. The patient posterior cornea element surface is adjacent to the anterior chamber of the patient eye.

The number of patient cornea cuts may further include a patient side cut. The patient side cut extends in the patient cornea from a periphery, in particular a circumferential edge, of the patient anterior lamellar cut towards the patient posterior cornea surface in a circumferentially closed manner. The patient side cut defines, at least in part, a circumferential patient cornea element surface.

The number of patient cornea cuts may further include a patient access cut. The patient access cut extends in the patient cornea from the patient side cut a to a peripheral region of the patient anterior cornea surface. The patient access cut forms an access passage in the patient cornea.

The patient cornea cut pattern may further define a patient cornea interlocking structure. The patient cornea interlocking structure is configured to interlock the patient cornea with a cornea implant after replacing the patient cornea element by the cornea implant.

In a further aspect, the present disclosure concerns an ophthalmological manufacture apparatus for manufacturing from a donor cornea a cornea implant. The manufactured cornea implant is suited for use in in posterior lamellar keratoplasty, the ophthalmological manufacture apparatus may include a manufacture laser device for implementing cornea cuts. The ophthalmological manufacture apparatus may further include a computerized manufacture control device in operative coupling with the manufacture laser device. The manufacture control device is designed to control the manufacture laser device to implement a number of donor cornea cuts. The donor cornea cuts form, in combination, a donor cornea cut pattern. A geometry of the cornea implant is defined by the donor cornea cut pattern.

The number of donor cornea cuts includes a donor anterior lamellar cut. The donor anterior lamellar cut extends in the donor cornea at a donor anterior lamellar cut distance from a donor posterior cornea surface of the donor cornea, the donor anterior lamellar cut defining a cornea implant anterior surface. A cornea implant posterior surface is generally defined by the portion of the donor posterior conceal surface which is delimited respectively circumscribed by the donor side cut.

The number of donor cornea cuts further includes a donor side cut. The donor side cut extends in the donor cornea from the donor anterior lamellar cut towards the donor posterior cornea surface in a circumferentially closed manner. A junction of the donor side cut and the donor anterior lamellar cut is displaced with respect to a circumferential edge, of the donor anterior lamellar cut. The donor side cut defines, at least in part, a circumferential cornea implant surface.

The number of donor cornea cuts may further include a donor access cut. The donor access cut extends from a periphery, in particular a circumferential edge, of the donor anterior lamellar cut to a donor anterior cornea surface.

The donor cornea cut pattern may further define a cornea implant interlocking structure. The cornea implant interlocking structure is configured to interlock the patient cornea with the cornea implant after replacing the patient cornea element by the cornea implant.

In a further aspect, the present disclosure concerns a method for manufacturing from a donor cornea a cornea implant suited for use in in posterior lamellar keratoplasty, in particular using an ophthalmological manufacture apparatus according in accordance with the present disclosure. The method may include implementing by means of a laser device a number of donor cornea cuts. The donor cornea cuts form, in combination, a donor cornea cut pattern. A geometry of the cornea implant may be defined by the donor cornea cut pattern. The laser device may in particular be a manufacture laser device of a manufacture apparatus in accordance with the present disclosure.

The number of donor cornea cuts includes a donor anterior lamellar cut. The donor anterior lamellar cut extends in the donor cornea at a donor anterior lamellar cut distance from a donor posterior cornea surface. The donor anterior lamellar cut defines a cornea implant anterior surface.

The number of donor cornea cuts further includes a donor side cut. The donor side cut extends in the donor cornea from the donor anterior lamellar cut towards the donor posterior cornea surface in a circumferentially closed manner. A junction of the donor side cut and the donor anterior lamellar cut is displaced with respect to a circumferential edge, of the donor anterior lamellar cut. The donor side cut defines at least in part, a circumferential cornea implant surface.

The number of donor cornea cuts further includes a donor access cut. The donor access cut extends from a periphery, in particular a circumferential edge, the circumferential edge of the donor anterior lamellar cut to a donor anterior cornea surface.

The donor cornea cut pattern may further define a cornea implant interlocking structure. The cornea implant interlocking structure is configured to interlock a patient cornea with the cornea implant after replacing the patient cornea element by the cornea implant. In a further aspect, the present disclosure concerns an ophthalmological surgical method for replacing a patient cornea element with a cornea implant by way of posterior lamellar keratoplasty. The method may in particular be carried out using an ophthalmological treatment apparatus in accordance with the present disclosure.

The ophthalmological surgical method includes implementing by means of a laser device, in particular an ophthalmological laser device, a number of patient cornea cuts. The patient cornea cuts form, in combination, a patient cornea cut pattern. A geometry of the patient cornea element is defined by the patient cornea cut pattern. The laser device may be a treatment laser device and/or ophthalmological laser device in accordance with the present disclosure.

The number of patient cornea cuts includes cuts as described above in the context of an ophthalmological treatment apparatus above as well as particular embodiments of such apparatus as discussed further below.

The ophthalmological surgical method includes, subsequent to resecting the patient cornea element respectively implementing the patient cornea cuts, removing the patient cornea element from the patient cornea, in particular via the patient access, cut, thereby creating a patient cornea cavity in the patient cornea. Removing the patient cornea element may include inserting forceps into patient access cut and grasping the patient cornea element.

The ophthalmological surgical method includes placing the cornea implant in the patient cornea cavity, in particular via the patient access cut, in particular using for example an insertion spatula.

It is noted that the patient cornea element and the corresponding patient cornea cavity as well as the cornea implant are of generally the same shape and generally identical dimensions.

The ophthalmological surgical method further includes interlocking the cornea implant with the patient cornea by engagement of a patient cornea interlocking structure of the patient cornea with a cornea implant interlocking structure of the cornea implant.

In a further aspect, the present disclosure concerns a cornea implant. The cornea implant may in particular be manufactured using an ophthalmological manufacture apparatus in accordance with the present disclosure and/or a manufacture method in accordance with the present disclosure. In an embodiment, a cornea implant in accordance with the present disclosure is made from tissue of a donor cornea.

The cornea implant includes a curved, in particular spherically curved, cornea implant anterior surface. The cornea implant further includes a curved cornea implant posterior surface which is displaced with respect to the cornea implant anterior surface in a posterior direction.

The cornea implant further includes a circumferential cornea implant surface. The circumferential cornea implant surface extends between a periphery, in particular a circumferential edge, of the cornea implant anterior surface and a periphery, in particular a circumferential edge, of the cornea implant posterior surface.

The cornea implant further includes a cornea implant interlocking structure. The cornea implant interlocking structure is configured to interlock a patient cornea with the cornea implant after replacing a patient cornea element of a patient cornea with the cornea implant. The cornea implant interlocking structure may in an embodiment be arranged at and/or forms part of the cornea implant posterior surface.

The patient cornea element is the piece of the patient cornea that shall be replaced by a cornea implant in posterior lamellar keratoplasty. Posterior lamellar keratoplasty in accordance with the present disclosure is particularly favorable since the patient access cut allows an easy removal of the patient cornea element and subsequent insertion of the cornea implant in a comparatively easy and safe manner with minimal risk of causing unintentional damage of the cornea as well as complications in general. By the patient access cut extending to the peripheral region of the patient anterior cornea surface, it the patient cornea element can be pulled out, e.g. using forceps, in a substantially linear movement and without exerting excessive stress on the tissue of the cornea. After removal of the resected patient cornea element, a patient cornea cavity is present in the patient cornea with a shape that generally corresponds to the patient cornea element. A cornea implant of generally the same shape may subsequently be inserted respectively placed in the patient cornea cavity in the same way, i.e. via the patient access cut.

A further advantage of posterior lamellar keratoplasty in accordance the present disclosure is in some embodiments the provision of a cornea implant at the cornea implant posterior surface. The patient cornea interlocking structure may be complementary to the cornea implant interlocking structure, thereby allowing a form fit Such interlocking structure allows efficient and safe establishment of an interlocking between cornea implant and patient cornea and in particular prevents the resected patient cornea element as well as the cornea implant from falling into the adjacent anterior chamber of the patient eye during manipulation. As will be explained in more detail below, the patient cornea interlocking structure supports the patient cornea element after implementing the patient cornea cuts before it is removed, and further supports the cornea implant upon being placed in the patient cornea cavity. Also, posterior lamellar keratoplasty in accordance the present disclosure avoids the need for sutures. Further advantages of particular embodiments are discussed further below in their respective context.

The patient anterior lamellar cut is defined by a closed and spatially curved, for example spherically curved, cut surface that is delimited by a circumferential edge. Typically, a patient cornea axis extends through a center of the patient anterior lamellar cut as axis of rotational symmetry. The patient anterior lamellar cut is generally smooth. For the patient anterior lamellar cut being spherically curved, the circumferential edge of the patient anterior lamellar cut is generally circular.

The patient cornea axis is generally a central axis respectively axis of symmetry of the patient cornea and of the patient cornea element that is resected. It generally corresponds to the optical axis of the patient eye. Similarly, the donor cornea axis is a central axis respectively axis of symmetry of the donor cornea and corresponds to the cornea implant axis of a cornea implant manufactured from the donor cornea. In a viewing direction transverse to the respective axis, the patient cornea element and the cornea implant are generally circular or substantially circular.

A patient posterior cornea element surface is generally defined by the portion of the patient posterior cornea surface which is delimited respectively circumscribed by the patient side cut. In an embodiment where the circumferential edge of the patient anterior lamellar cut is circular as mentioned, the patient side cut may for example have the shape of a tubular ring that may extend parallel to the patient cornea axis. Designs, however, are also possible, e.g. with the circumferential edge of the patient anterior lamellar cut being angled with respect to the patient cornea axis. The same applies in an analog manner for the donor and the cornea implant.

The patient anterior cornea element surface and the patient posterior cornea element surface (forming part of the patient posterior cornea surface) are generally spaced apart with respect to each other along the patient cornea axis. Similarly, the cornea implant anterior surface and the cornea implant posterior surface (forming part of the donor posterior cornea surface when manufactured from a donor cornea) are generally spaced apart with respect to each other along the cornea implant axis respectively the donor cornea axis.

The patient anterior lamellar cut and the donor anterior lamellar cut are generally spatially curved, in particular in a spherically curved, with the patient cornea axis respectively donor cornea axis as axis of symmetry. The same applies, in an analogue manner, to the donor and to the cornea implant.

In dependence of the desired shape of the cornea implant, the patient anterior lamellar cut distance may be constant over the patient anterior lamellar cut, or may vary over the patient anterior lamellar cut. It may in particular vary in a radial manner with respect to the patient cornea axis. The same applies in an analogue manner for the donor anterior lamellar cut distance.

As mentioned before, the shape and dimensions of the patient cornea element, respectively the patient cornea cavity after removal of the patient cornea element generally correspond to the shape and geometry of the cornea implant and the cornea cuts may be implemented accordingly in the donor cornea and the patient cornea. In particular, the patient anterior lamellar cut may be identical or substantially identical to the donor anterior lamellar cut, and the patient side cut may be identical or substantially identical to the donor side cut. Similar, a patient posterior lamellar cut as present in an embodiment as discussed further below may be identical or substantially identical to a donor posterior lamellar cut. A patient auxiliary side cut as present in an embodiment as discussed further below may be identical or substantially identical to a donor auxiliary side cut.

However, some deviation may be present between patient and donor cuts in dependence of the specific situation. By way of example, a donor auxiliary side cut may have an extension that slightly differs from the corresponding patient auxiliary side cut. Similarly, a donor posterior lamellar cut may somewhat differ the patient posterior lamellar cut, and/or donor side cut may somewhat differ the patient side cut. A donor cut may in particular be longer respectively wider or narrower respectively shorter as comparted to the corresponding patient cut. Such intentional differences between donor cut and side cuts may be used to avoid interference between tissue implant and patient cornea as well as to ensure correct positioning and fitting.

The patient access cut may meet the patient side cut at the junction of the patient side cut and the patient anterior lamellar cut. The patient access cut, however, may also meet the patient side cut displaced in posterior direction with respect to the junction of the patient side cut and the patient anterior lamellar cut.

Further, the patient cornea interlocking structure and cornea implant interlocking structure are generally complementary to each other. In an embodiment, the patient cornea interlocking structure is defined, at least in part, by a patient posterior cornea element surface. Such embodiments are discussed further below in more detail.

Alternatively, or additionally however, the interlocking structures may be arranged fully or partly at the circumference respectively circumferential surface of the patient cornea cavity and the cornea implant, respectively. In particular, the circumference surface of the patient cornea cavity and the cornea implant may include complementary positive respectively convex and negative respectively concave interlocking features that are designed for mutual engagement. Positive interlocking features may, for example, be formed by protrusions such as circumferential rims or tabs, and negative interlocking features may be formed by recesses or cutouts. Further the circumferential surface of the patient cornea cavity and the cornea implant may extend between proximal and distal with complimentary zig-zag shapes. In embodiments where the interlocking structures are circumferentially arranged, the patient side cut and the donor side cut are generally no smooth and continuous cuts, but are segmented in order to provide the patient cornea cavity interlocking structure and cornea implant interlocking structure.

In an embodiment, the treatment control device may be configured to receive patient cut information, the patient cut information defining the patient cornea cut pattern. Similarly, a manufacture control device may be may be configured to receive donor cut information, the patient cut information defining the donor cornea cut pattern.

The patient cut information and/or donor cut information may be received, for example, via a data interface from a further device or on a data carrier, such as a CD-ROM, or may be acquired by an ophthalmologic measurement device in operative coupling with the treatment control device or manufacture control device, respectively an ophthalmological manufacture and treatment control device.

According to a further aspect, the present disclosure concerns a computer program product including a non-transient computer readable medium having stored therein computer program code. The computer program code is configured to direct a processor of a computerized treatment control device of an ophthalmological treatment apparatus to control a treatment laser device of the ophthalmological treatment apparatus to implement a number of patient cornea cuts, the patient cornea cuts forming, in combination, a patient cornea cut pattern. The number of patient cornea cuts respectively the patient cornea cut pattern may correspond to any embodiment as discussed above and/or further below in the context of an ophthalmological treatment apparatus and/or ophthalmological manufacture and treatment apparatus.

According to a further aspect, the present disclosure concerns a further computer program product including a non-transient computer readable medium having stored therein computer program code. The computer program code is configured to direct a processor of a computerized manufacture control device of an ophthalmological manufacture apparatus to control a manufacture laser device of the ophthalmological manufacture apparatus to implement a number of donor cornea cuts, the donor cornea cuts forming, in combination, a donor cornea cut pattern. The number of donor cornea cuts respectively the donor cornea cut pattern may correspond to any embodiment as discussed above and/or further below in the context of an ophthalmological manufacture apparatus and/or ophthalmological manufacture and treatment apparatus.

In an embodiment, the treatment control device is configured to control the treatment laser device to implement the patient anterior lamellar cut subsequent to the patient side cut and the patient access cut subsequent to the patient anterior lamellar cut. Also, in an embodiment, the manufacture control device is configured to implement the donor anterior lamellar cut subsequent to the donor side cut and the donor access cut subsequent to the donor anterior lamellar cut.

In an embodiment, the patient side cut does not extend to the patient posterior cornea surface. Further, the patient cornea cut pattern may include a patient posterior lamellar cut. The patient posterior lamellar cut extends circumferential in the patient cornea from a posterior end, in particular a posterior edge, of the patient side cut inwards with respect to the patient cornea, in particular with a constant distance to the patient anterior lamellar cut. The patient cornea cut pattern may for this type of embodiment further include a patient auxiliary side cut. The patient auxiliary side cut extends from an inner periphery, in particular an inner edge, of the patient posterior lamellar cut to the patient posterior cornea surface.

Further in an embodiment, the donor side cut does not extend to the donor posterior cornea surface. The donor cornea cut pattern may include a donor posterior lamellar cut. The donor posterior lamellar extends in the donor cornea from a posterior edge of the donor side cut inwards with respect to the donor cornea, in particular with a constant distance to the donor anterior lamellar cut. The donor cornea cut pattern may further include a donor auxiliary side cut. The donor auxiliary side cut extends from an inner edge of the donor posterior lamellar cut to the donor posterior cornea surface.

It is noted that the patient cornea element and the corresponding patient cornea cavity and the cornea implant are of generally the same shape and generally identical dimensions. Therefore, considerations and embodiments for the patient cornea cut pattern, in particular a patient posterior lamellar cut and patient auxiliary side cut generally hold true for the donor cornea cut pattern, in particular a donor posterior lamellar cut and donor auxiliary side cut, in an analogue manner.

In an embodiment with a patient posterior lamellar cut, a part of the patient cornea element that is delimited in posterior direction by the patient posterior lamellar cut is referred to as peripheral part, while the part that is in posterior direction delimited by the patient posterior cornea surface is referred to as inner or central part. Generally, peripheral part of the patient cornea element circumferentially surrounds the inner or central part. The same applies in an analog manner for the donor and the cornea implant.

In an embodiment, the patient posterior lamellar cut is shaped in the same or substantially the same manner as the patient anterior lamellar cut and may, e.g., also be spherical. Further, the patient posterior lamellar cut may extend with a generally uniform respectively constant distance to the patient anterior lamellar cut. In alternative embodiments, the patient posterior lamellar cut may e.g., be planar and extend either transverse, in particular normal, or oblique to the patient cornea axis. For an oblique patient posterior lamellar cut, the peripheral part of the patient cornea element and accordingly also the cornea implant may be tapered respectively frustoconical and be thicker at the periphery as comparted to the transition to the inner or central part. Further designs of the patient posterior cornea surface apart from planar or spherical are possible as well.

In an embodiment, the patient cornea element includes a circumferential step in a patient posterior cornea element surface, in particular in a peripheral region of the patient posterior cornea element surface. In an embodiment of the cornea implant, the cornea implant posterior surface includes a circumferential step in a cornea implant posterior surface, in particular in a peripheral region of the cornea implant posterior surface. As will be explained in the following, such embodiments are particularly favorable for interlocking the cornea implant with respect to the patient cornea by way of complementary structures.

The patient posterior lamellar cut and the patient auxiliary side cut result for such type of embodiment in a peripheral step being formed in the patient cornea element at the patient posterior cornea element surface. Similarly, the donor posterior lamellar cut and the donor auxiliary side cut result in a peripheral step being formed in the cornea implant at the cornea implant posterior surface. The step may in particular include a circumferential recess that extends laterally respectively radially from the patient auxiliary side cut to the circumferential or outer edge of the patient cornea element, respectively from the donor auxiliary side cut to the circumferential or outer edge of the cornea implant. The patient posterior lamellar cut and the donor posterior lamellar cut may in particular be annular cuts.

For such embodiment, a central part of the patient posterior cornea element surface around the patient cornea axis may directly formed by the patient posterior cornea surface as is was prior to implementing the patient cornea cuts. A peripheral part of the patient posterior cornea element surface is defined by the patient posterior annular cut. Similarly, a central part of the cornea implant posterior surface around the donor cornea axis respectively the cornea implant axis may be directly formed by the donor posterior cornea surface as is was prior to implementing the donor cornea cuts. A peripheral part of the cornea implant posterior surface may be defined by the donor posterior lamellar cut. The central and the peripheral part of the patient posterior cornea element surface and the cornea implant posterior surface are separated via the patient auxiliary side cut respectively the donor auxiliary side cut.

The thickness of the patient cornea element respectively the distance between the patient anterior cornea element surface and the patient posterior cornea element surface may be larger for the inner or central part of the patient cornea element as compared to the outer or peripheral part. Similarly, the thickness of the cornea implant respectively the distance between the cornea implant anterior surface and the cornea implant posterior surface may be larger for the inner or central part of the cornea implant as compared to the outer or peripheral part.

For such embodiment, a lateral respectively radial extension of the step or recess in the patient cornea element is determined by respectively corresponds to the patient posterior lamellar cut, while a longitudinal extension of the step or recess in the patient cornea element is determined by respectively corresponds to the patient auxiliary side cut. Similarly, a lateral respectively radial extension of the step or recess in the cornea implant is determined by respectively corresponds to the donor posterior lamellar cut, while a longitudinal extension of the step or recess in the cornea implant is determined by respectively corresponds to the donor auxiliary side cut.

After removing the patient cornea element from the patient cornea in the before-explained type of embodiment, a patient cornea tissue ring will extend into the patient cornea cavity at the posterior side of the patient cornea cavity at the boarder to the anterior chamber. The thickness of the patient cornea tissue ring is determined respectively corresponds to the extension respectively length of the patient auxiliary side cut, while its radial respectively lateral extension is determined by respectively corresponds to the extension of the patient posterior lamellar cut. When placing the cornea implant in the patient cornea cavity, the cornea implant interlocking structure, in particular a recess as defined for example by a posterior lamellar cut and donor auxiliary side cut as mentioned before engages the patient cornea tissue ring, thereby interlocking the cornea implant with the patient cornea and in particular preventing the cornea implant form falling into the anterior chamber. When the cornea implant is positioned, the peripheral part of the cornea implant posterior surface contacts respectively abuts the anterior surface of the patient cornea tissue ring and the cornea implant rests on the patient cornea tissue ring.

Where the patient posterior lamellar cut extends in a constant distance to the patient anterior lamellar cut, it generally has a corresponding contour and may, for example be spherically curved. Similarly, where the donor posterior lamellar cut extends in a constant distance to the donor anterior lamellar cut, it generally has a corresponding contour. In alternative embodiment, however, the patient posterior lamellar cut and the donor posterior lamellar cut may in each case have a contour that differs from the contour of the respective anterior cut. Bay way of example, the patient posterior lamellar cut and the donor posterior lamellar cut may be flat respectively planar. In a further embodiment, the patient posterior annular cut may for example be corrugated. In any case, the contour of the patient posterior lamellar cut and the donor posterior lamellar may have an identical or substantially identical contour, resulting in the peripheral portion of the posterior cornea implant matching respectively being complementary to the anterior surface of the patient cornea tissue ring, thereby ensuring an aerial contact respectively a contact over their full surface.

In an embodiment, the treatment control device is configured to control the treatment laser device to implement the patient posterior lamellar cut subsequent to the patient auxiliary side cut and prior to the patient side cut. This type of embodiment is favorable regarding an efficient and precise implementation of the patient cornea cuts. Similarly, the manufacture control device may be configured to control the manufacture laser device to implement the donor posterior lamellar cut subsequent to the donor auxiliary side cut and prior to the donor side cut.

In an embodiment, the patient access cut meets the patient anterior cornea surface in an acute angle. Such arrangement is favorable for removing the patient cornea element and subsequently inserting the cornea implant I a smooth manner and a shallow angle with respect to the patient anterior cornea surface.

In an embodiment, the patient cornea cut pattern includes an auxiliary patient access cut. The auxiliary patient access cut extends in the patient cornea from the patient side cut to the peripheral region of the patient anterior cornea surface. The auxiliary patient access cut is arranged with respect to a circumference of the patient side cut opposite to the patient access cut. The auxiliary patient access cut forms an auxiliary access passage in the patient cornea. In a view along the patient cornea axis, the auxiliary patient access cut and the patient access cut may be diametrically opposed to each other. In an embodiment, the patient auxiliary access cut meets the patient anterior cornea surface in a perpendicular or substantially perpendicular manner.

The auxiliary patient access cut may meet the patient side cut at the posterior edge of the patient side cut, respectively in some embodiments a mentioned before at the junction of the patient side cut and the patient posterior lamellar cut. The auxiliary patient access cut, however, may also meet the patient side cut displaced in anterior direction respectively displaced in direction towards the patient anterior lamellar cut with respect to the posterior edge of the patient side cut.

Providing an auxiliary patient access cut in addition to the patient access cut as mentioned before is favorable regarding the insertion and positioning of the cornea implant in the patient cornea cavity. Subsequent to placing the cornea implant in the patient cornea cavity as mentioned before, the cornea implant may additionally be grasped by a favorably serrated auxiliary forceps that is inserted into the auxiliary patient access cut. By maneuvering the cornea implant with an insertion spatula as well as the auxiliary forceps, it may be placed in the correct position. In particular, the auxiliary forceps may be used to the pull the patient cornea implant into position.

In an embodiment, the treatment control device is configured to the patient the patient cornea cuts that define the geometry of the patient cornea element in sequence one after the other. Similarly, the manufacture control device may be configured to implement the donor cornea cuts that define the geometry of the cornea implant in sequence one after the other. These types of embodiments are particularly favorable regarding precision and efficiency. In particular, the end of each of such cuts corresponds at the same time to the beginning of a next following cut.

In any case, the patient cornea cuts as well as the tissue cornea cuts are implemented in an order and with cutting direction that ensures that no shading occurs when implementing any cut as a result from previous cuts. This generally implies an implementation of the cuts from posterior (first) to anterior.

Regarding the ophthalmological treatment apparatus and the ophthalmological manufacture apparatus, it is noted that they may be different and distinct apparatuses which may also be present at different locations. Alternatively, however, they may be partly or fully integrated as combined ophthalmological manufacture and treatment apparatus. The computerized treatment control device may be integral with a computerized manufacture control device, respectively an ophthalmological manufacture and treatment control device may be both a computerized treatment control device and a computerized manufacture control device.

Similarly, the treatment laser device may be integral with a manufacture laser device, respectively an ophthalmological laser device may be both a treatment laser device and a manufacture laser device.

Where not explicitly stated differently, expressions related to components of an apparatus may refer to an ophthalmological treatment apparatus, an ophthalmological manufacture apparatus or an ophthalmological manufacture and treatment apparatus. In particular, the expression "control device" may generally refer to a treatment control device, a manufacture control device or an ophthalmological manufacture and treatment control device as mentioned. Similarly, the expression "ophthalmological laser device" may refer to a treatment laser device, manufacture laser device or a combined treatment and manufacture laser device. Typically, the same kinds of laser devices may be used for both manufacture of the cornea implant as well as resecting the patient cornea.

An ophthalmological laser device may in an embodiment include femtosecond laser source. A femtosecond laser source is particularly favorable in that it allows to implement the cornea cuts with high precision and reproducibility. Nano or picosecond laser in the UV range may be used in alternative embodiments.

A method for manufacturing a cornea implant in accordance with the present disclosure a method for manufacturing from a donor cornea may include, prior to implementing donor cornea cuts, mounting the donor cornea on an artificial anterior chamber epithelium with the donor anterior cornea surface facing the manufacture laser device respectively ophthalmological laser device and applanating the donor cornea with a sterilized contact element.

Similarly, an ophthalmological surgical method in accordance with the present disclosure may include, prior to implementing patient cornea cuts, applanating the patient cornea with a sterilized contact element.

The donor access cut is generally a circumferential cut respectively extends circumferentially from a circumferential edge of the donor anterior lamellar cut as mentioned before. In an embodiment, the donor access cut is circumferentially closed. In such embodiment, the method for manufacturing the cornea implant may further include, subsequent to implementing the donor cornea cuts, lifting off or peeling off a donor cover element, the donor cover element being a portion of the donor cornea delimited by the donor anterior cornea surface, the donor anterior lamellar cut and the donor side cut. The donor cover element is the portion of the donor cornea anterior of the cornea implant, with the cornea implant and the donor cover element being separated by the donor anterior lamellar cut.

Alternatively, however, the donor access cut is not circumferentially closed but extends only over a portion of the circumference of the donor anterior lamellar cut. In this case, the donor cover element remains connected to the further tissue of the donor cornea via a tissue bridge after implementing the donor cornea cuts, in particular the donor anterior lamellar cut and the donor access cut. In such case, the method may include flipping the donor cover element away along the tissue bridge, with the tissue bridge serving as hinge.

The method may further include grasping the cornea implant, in particular using forceps, and removing it from the donor cornea.

BRIEF DESCRIPTION OF THE FIGURES

The herein described disclosure will be more fully understood from the detailed description given herein below and the accompanying drawings which should not be considered limiting to the disclosure described in the appended claims. The drawings show:

EXEMPLARY EMBODIMENTS

Figure 1:
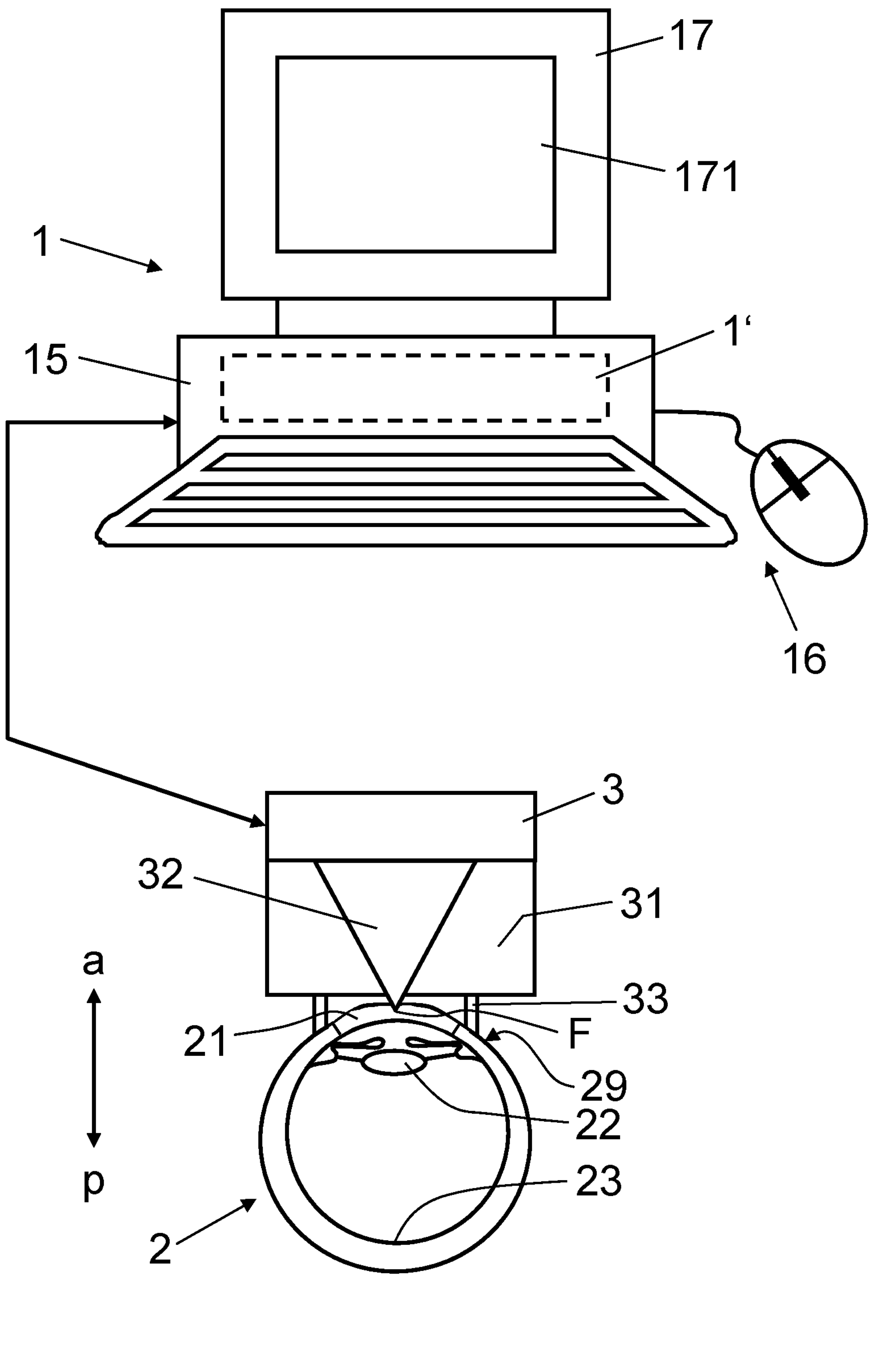
FIG. 1 illustrates an embodiment of an ophthalmological treatment and manufacture apparatus according to the present disclosure in a schematic sectional view.

In the following, reference is first made to FIG. 1. FIG. 1 shows an exemplary embodiment of an ophthalmological treatment and manufacture apparatus 1, 3 in accordance with the present disclosure and in interaction with a human eye (patient eye) 2 in a schematic view.

For the human eye 2, the cornea 21, the lens 22, the retina 23 and the sclera 29 are shown. Further, the limbus (not separately referenced) is present as transition area between the cornea 21 and the sclera 29.

In FIG. 1 as well as further figures, an anterior-pointing direction is indicated by "a" and a posterior-pointing direction is indicated by "p". The anterior-pointing direction a and the posterior-pointing direction p are defined in the same manner for the patient eye 2 as well as its parts, as well as a donor cornea and a cornea implant as illustrated in further figures below.

The ophthalmological treatment and manufacture apparatus comprises the computerized ophthalmological treatment and manufacture control device 1 (in the following generally referred to as control device) and the ophthalmological laser device 3 (in the following generally referred to as laser device) that is exemplarily based on a femtosecond laser source in operative coupling with a projection lens that is part of an application head (components as laser sources, scanners and beam delivery and shaping optics are not separately shown).

From the laser device 3 respective its projection lens, laser radiation is emitted and focused onto a point of the patient cornea 21 (indicated by radiation cone 32), or similarly, of a donor cornea. In a situation of use, laser device 3 is coupled to the patient eye 2 or a donor cornea via a patient interface 31 that is typically designed for one-way use and couples with the surgical laser device 3 respectively its application head via releasable mechanical coupling and for coupling with the eye 2 respective its sclera 29 and/or cornea 21 via a suction ring 33. Coupling is not mandatory if the laser can compensate for eye movement or is fast enough. The patient interface 31 may be designed to deform the eye surface to a desired shape for the surgical procedure, e. g. planar, spherical or aspherical shape with an applanation-type coupling and a transparent contact element. Alternatively, the patient interface 31 may be designed to couple with the patient eye 2, in particular the patient cornea 21, or a donor cornea, via a contact liquid, e. g. saline solution, substantially without causing deformation. An exemplary patient interface is disclosed in the EP2853247.

The control device 1 is exemplarily shown as being based on a general-purpose computing device 15, such as a PC or workstation, in operative coupling with a user interface that includes an input unit 16 (shown with a keyboard and a mouse for exemplary purposed) and an output unit 17 (exemplarily shown as computer monitor with an image area 171. Other devices for the input unit 16 and/or the output unit 17 may be used as well. For example, the input unit 16, may include a track ball and/or a touch pad. The output unit 17 may, for example, be or include a beamer or glasses with integrated display, to be worn by an operator.

The control device 1 includes a number of functional modules 1', which include interface circuitry for coupling with the laser device 3 via an (typically electrical) operative coupling. The control device 1 further includes one or more processors, e. g. microprocessors and/or microcontrollers for controlling operation of the control device 1 and the ophthalmological treatment and manufacture apparatus as a whole in accordance with corresponding program code. The control device 1 further includes volatile and/or non-volatile memory that store program code and/or data.

In FIG. 1, the control device is 1 shown as a compact unit. The control device 1 may, however, also be distributed between a number of computing devices, each with particular functional units 1'. The computing devices may be coupled via data interfaces such as a LAN network or USB connection for data transfer and/or between which data may be transferred via physical media, such as CD-ROMS, DVDs, magnetic storage discs, or the like. Further, the control device 1 may be fully or partly integrated with the surgical laser device 3.

It is noted that rather than an ophthalmological treatment and manufacture apparatus, a dedicated and distinct ophthalmological treatment apparatus and ophthalmological manufacture apparatus may be used as explained in the general description to be used. While typically deviating regarding the program code and/or data, a distinct ophthalmological treatment apparatus and an ophthalmological manufacture apparatus may in each case generally be designed as depicted in FIG. 1.

Figure 2:
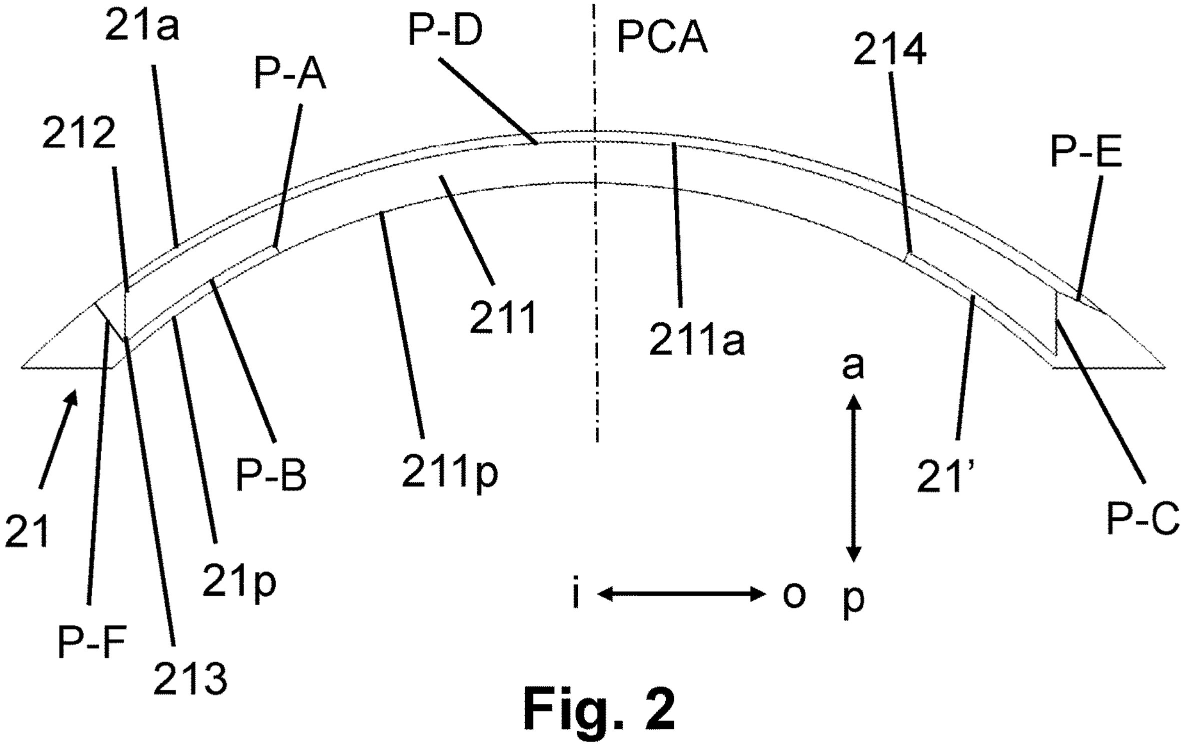
FIG. 2 illustrates a patient cornea with implemented patient cornea cuts according to an embodiment of the present disclosure in a schematic sectional side view.
Figure 3:
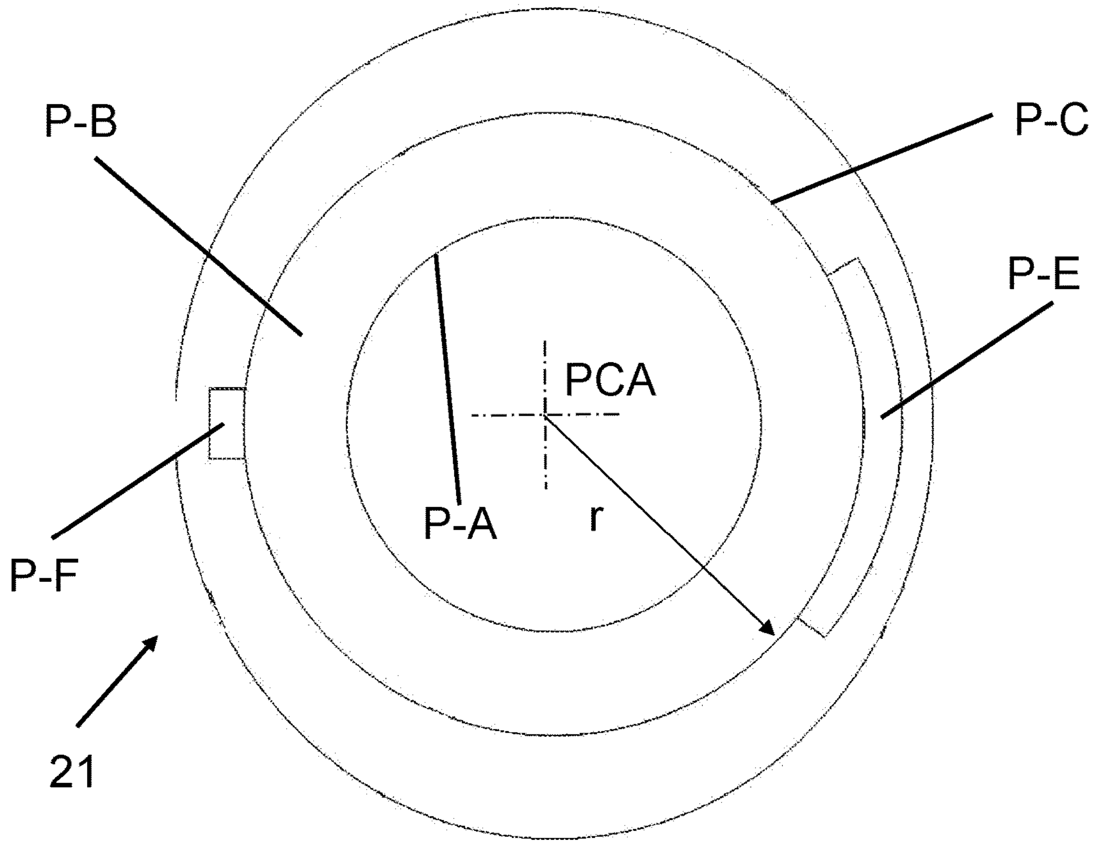
FIG. 3 illustrates the patient cornea with implemented patient cornea cuts corresponding to FIG. 2 in a schematic top view.
Figure 4:
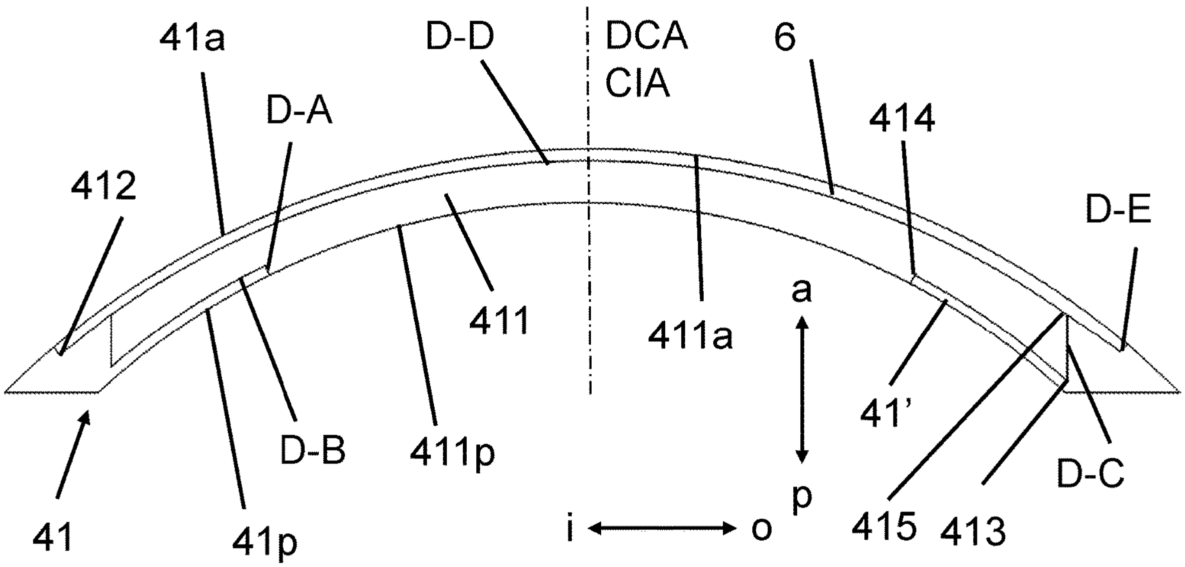
FIG. 4 illustrates a donor cornea with implemented donor cornea cuts according to an embodiment of the present disclosure in a schematic sectional side view.
Figure 5:
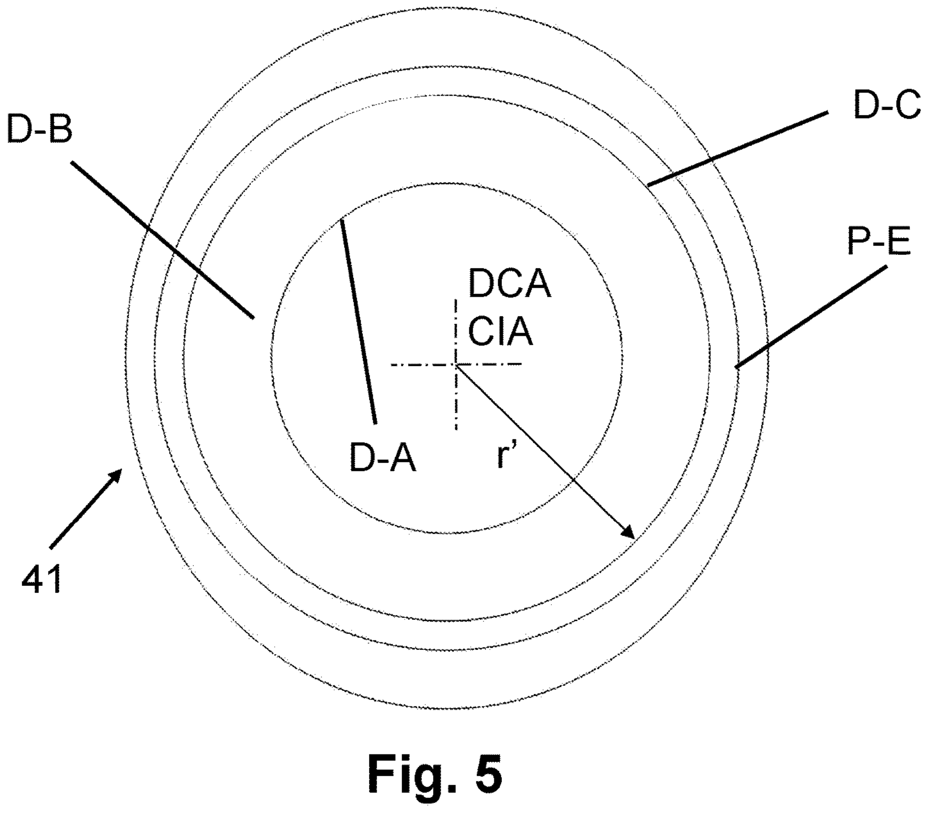
FIG. 5 illustrates the donor cornea with implemented donor cornea cuts corresponding to FIG. 4 in a schematic top view.

In the following, reference is additionally made to FIG. 2 and FIG. 3. FIG. 2 shows a schematic sectional side view of the patient cornea 21 with the patient cornea element 211 and the patient cornea cuts respectively patient cornea cut pattern as described in the following. FIG. 3 shows a corresponding schematic top view of the patient cut pattern. The patient cornea axis is referenced with "PCA". It is noted that like in further figures as discussed below, in particular FIG. 4, hatchings are omitted for clarity reasons. Further it is noted that the top views of FIG. 3 and FIG. 5 are shown somewhat smaller as compared to the side sectional views of FIG. 2 and FIG. 4. It is noted that the figures generally show the cornea and cornea cuts in their natural shape, i.e. without applanating, for clarity reasons. Also references to the geometry of particular elements or cuts are made with reference to this configuration, if not stated differently.

An anterior-pointing respectively posterior-pointing direction is referenced with "a" respectively "p". An inwards-pointing direction (towards a center of the patient cornea 21) is referenced with "i" and an outwards-pointing direction (towards the periphery of the patient cornea 21) is referenced with "o". The same notation is used in further figures below for the donor cornea and the cornea implant in an analogue manner. It is noted that the inwards-pointing direction I and the outwards-pointing direction o are radial respectively lateral directions. It is noted in this context that the patient cornea, the donor cornea as well as the cornea implant are here generally assumed as rotationally symmetric, which is typically approximately but not necessarily strictly the case in practice.

The patient anterior lamellar cut P-D extends in the patient cornea 21 and approximately equidistant to the patient anterior cornea surface 21 and has for example a diameter of about 10 mm. The patient anterior lamellar cut P-D lies fully within the patient cornea 21 between the patient anterior cornea surface 21*a* and the patient posterior cornea surface 21*p*. The patient anterior lamellar cut P-D extends in a substantially equidistant manner to the patient anterior cornea surface 21*a* as well as in substantially equidistant manner to the patient posterior cornea surface 21*p*. Typically, the patient anterior lamellar cut P-D is further substantially spherical and centered with respect to the patient cornea axis PCA. The patient anterior lamellar cut P-D is spaced apart from the patient anterior cornea surface 21*a* by about 100 micrometer or somewhat more in a typical embodiment. The same applies for the distance between the donor anterior lamellar cut D-D and the donor cornea surface as discussed further below. Generally, a small distance between the patient respectively donor anterior cornea surface and the patient respectively donor anterior side cut is preferably, without, while ensuring that a sufficient amount of tissue remains, in particular at the patient cornea, to ensure stability respectively avoid damage of the cornea tissue anterior of the patient cornea element.

The patient side cut P-C is a circumferential cut and extends from the circumferential edge 212 of the patient anterior lamellar cut towards P-D towards the patient posterior cornea surface 21*p* in a circumferentially closed manner. In the shown embodiment, the patient side cut P-C is for example an inverted 150 degrees cut in the applanated state and may run substantially parallel to the patient cornea axis PCA, which however is not essential. In alternative embodiments, the patient side cut may be angled respectively oblique to the patient cornea axis PCA. In the shown design, the patient side cute P-C does not extend full to the patient posterior cornea surface 21*p*, bud ends within the patient cornea, spaced apart from the patient posterior cornea surface 21*p* for interlocking purposes as explained further below. It is noted that the circumferential edge 212 of the patient anterior lamellar cut is at the same time an anterior edge of the patient side cut P-C.

In the shown embodiment, a patient posterior lamellar cut P-B runs from the posterior edge 213 of the patient side cut P-C inwards. The patient posterior lamellar cut P-B extends in a circumferentially closed manner inward. In the shown embodiment, the patient posterior lamellar cut P-B extends with constant distance to the patient anterior lamellar cut P-D in a coaxial respectively centered manner and is preferably spherical. It is noted that the posterior edge 213 of the patient side cut P-C is at the same time a circumferential outer edge of the patient posterior lamellar cut P-B. Further, a patient auxiliary side cut P-A runs from a circumferential inner edge 214 of the patient posterior lamellar cut P-B to the patient posterior cornea surface 21*p* and extends to the posterior cornea surface 21*p*.

The patient anterior lamellar cut P-D, the patient posterior lamellar cut P-B and the patient posterior cornea surface 21*p* delimit, in combination, a patient cornea element 211 in axial respectively anterior-posterior-direction. Further, the patient side cut P-C and patient auxiliary side cut P-A delimit the patient cornea element 211 in the radial direction. Via patient cornea cuts P-A, P-B, P-C, P_D, the patient cornea element 211 is separated from the further tissue of the patient cornea 21. The patient cornea element 211 is formed by respectively comprises the generally pathological respectively defective portion of the patient cornea that is resected and subsequently replaced by a cornea implant. The patient anterior cornea element surface is defined by the patient anterior lamellar cut P-D, while the patient posterior cornea element surface 211*b* is defined by the patient posterior cornea surface 21*p* in a central part (in radial direction from the patient cornea axis PCA to the patient auxiliary side cut P-A), and by the patient posterior lamellar cut P-B in a peripheral part (in radial direction outwards from the patient auxiliary side cut P-A).

Via the patient posterior lamellar cut P-B and the patient auxiliary side cut P-A, an annular step is formed in the patient posterior cornea element surface 211_*p*, respectively an annular recess is formed at the posterior side of the patient cornea element 211. The portion of tissue that is separated from the patient cornea element 211 by the patient posterior lamellar cut P-B and the patient auxiliary side cut P-A is a patient cornea tissue ring 21' and is complementary to the recess in the patient cornea element 211.

In addition to the patient cornea cuts P-A, P-B, P-C, P-D which define, in combination the shape of the patient cornea element 211, the patient cornea cut pattern includes two additional patient cornea cuts that serve the surgical procedure, namely a patient access cut P-E and an auxiliary patient access cut P-F. A patient access cut P-E extends in the patient cornea 21 from the patient side cut P-C to a peripheral region of the patient anterior cornea surface 21*a*. In the shown design, the patient access cut P-E meets the patient side cut P-C at its anterior edge 212. It could, however, also meet the patient side cut P-C somewhat further posterior in direction towards its posterior edge 213. Favorably, the patient access cut P-E meets the patient anterior cornea surface in an acute respectively shallow angle. The patient access cut P-E may be implanted starting at the periphery anterior cornea surface 21*a* and ending at the patient side cut P-E.

In the shown embodiment, the patient access cute P-E meets the patient anterior cornea surface 21*a* as a circular arc and generally concentrically to the patient cornea axis PCA: This, however, is not essential. In alternative embodiments, the patient access cut P-E may meet patient anterior cornea surface 21*a* in a straight line or as outwards-curved arc, i.e. away from the patient cornea axis P-A.

As best visible in FIG. 3, the patient access cut is a sectoral cut that is not circumferentially thoroughgoing but extends over an arc length in a typical range of about 4 mm to 5 mm. The patient access cut P-E provides a tunnel-shaped access channel for removing the patient cornea element 211 as well as inserting and positioning the cornea implant. The patient access cut is favorably shaped to allow the insertion of an insertion spatula.

In the shown embodiment, an auxiliary patient access cut P-F is provided diametrically opposed to the patient access cut P-E. The auxiliary patient access cut P-F extends form the patient side cut P-C to the peripheral region of the patient anterior cornea surface 21*a*. In the shown design, the auxiliary patient access cut meets the patient side cut P-C at its posterior edge 213. It could, however, also meet the patient side cut P-C somewhat further anterior in direction towards its anterior edge 212. The auxiliary patient access cut P-F provides a tunnel-shaped auxiliary access channel for positioning the cornea implant with an auxiliary forceps that is introduced via the auxiliary patient access cut P-F.

While the patient cornea cuts may generally be implemented respectively executed in different orders, an advantageous order that is particularly favorable is P-A, P-B, P-C, P-D, P-E, P-F.

After removing the patient cornea element 211, a patient cornea cavity of generally same shape and dimension will be present in the patient cornea.

In the following, reference is additionally made to FIG. 4 and FIG. 5. FIG. 4 shows a schematic sectional side view of the donor cornea 41 from which the cornea implant 411 is manufactured respectively produced, as well as the donor cornea cuts respectively the donor cornea cut pattern. FIG. 5 shows a corresponding schematic top view of the donor cut pattern. The donor cornea axis is referenced with "DCA", generally corresponding to the cornea implant axis CIA which is referenced as CIA. Since a number of donor cornea cuts corresponds to patient cornea cuts as discussed before, the following description generally focusses on the differences and particular aspects of the manufacture of cornea implant 411.

The donor side cut D-C, the donor posterior lamellar cut D-B and the donor auxiliary side cut D-A generally correspond to the patient side cut P-C, the patient posterior lamellar cut P-B, and the patient auxiliary side cut P-A. The donor auxiliary side cut D-A, however, may have in a particular implementation have a somewhat smaller diameter in a viewing direction along the donor cornea axis DCA as compared to the patient auxiliary side cut P-A in a viewing direction along the patient cornea axis PCA, respectively the donor auxiliary side cut D-A may be somewhat closer to the donor cornea axis DCA than the patient auxiliary side cut P-A is to the patient cornea axis PCA. The distance between the patient anterior lamellar cut P-D to the patient posterior lamellar cut B-B is generally identical to the distance between the donor anterior lamellar cut D-D and the donor posterior lamellar cut D-B.

Further, the radial extension of the donor posterior lamellar cut D-B may in an embodiment be somewhat larger as compared to the patient posterior lamellar cut P-B. In this way, the radius r' (see FIG. 5) of the cornea implant 411 is slightly larger as compared to the radius r of the patient cornea element 211, respectively the lateral dimension of the cornea implant 411 is slightly larger respectively has a slight oversize as compared to the patient cornea element 211. In this way, it is ensured that the cornea implant sits snugly in the patient cornea cavity after insertion.

Other embodiments, however, may be used as well. In particular, the patient cornea cuts and the corresponding donor cornea cuts may correspond to each other as closely as possible.

Further, the lateral extension of the donor anterior lamellar cut D-D may in an embodiment be wider respectively the circumferential edge 412 of the donor anterior lamellar cut D-E as compared to the patient anterior lamellar cut P-D. As a consequence, the donor side cut D-C does not meet with the donor anterior lamellar cut D-D at its circumferential edge 412. Instead, the donor side cut D-C is displaced inwards and a junction of its anterior edge 415 with the donor anterior lamellar cut is displaced inwards respectively within the area as delimited by the circumferential edge 412 of the donor anterior lamellar cut D-D. Further, the donor access cut D-E is a circumferential cut that extends from the circumferential edge 412 to the donor anterior cornea surface 41*a*.

As a consequence of the here-described cut arrangement a donor cover element 6 is created that laterally projects over the cornea implant 6 that is manufactured via the donor cornea cuts. The donor cover element 6 is generally separated from the further parts of the donor cornea 41 via the donor anterior lamellar cut D-D and the donor access cut D-E. In the shown embodiment, the donor access cut is circumferentially closed respectively thronging. Subsequent to implementing the donor cornea cuts, the donor cover element 6 can be simply peeled or lifted off, using a suited instrument such as forceps. Subsequently, the manufactured cornea implant 411 can be removed from the remaining tissue of the donor cornea 41. In an alternative embodiment, the donor side cut D-E is not circumferential through going, but a tissue bridge remains via which the donor cover element 6 may be flipped away in a hinge-like manner to provide access to the cornea implant 411.

When inserting and positioning the cornea implant 411 in the patient cornea cavity of the patient cornea 41, the peripheral part of the cornea implant posterior surface 411*p* will abut the anterior surface of the patient cornea tissue ring 21' such that the cornea implant 411 rests on the patient cornea tissue ring 21'. In a variant, the cornea tissue ring 21' does not extend transverse to the patient cornea axis PCA respectively cornea implant axis CIA, but extend oblique, in particular in anterior direction. The circumferential recess of the cornea implant 411 is designed accordingly in this case. For the donor the same applies in an analogue manner.

While the donor cornea cuts may generally be implanted in different orders, an advantageous order that is particularly favorable is D-A, D-B, D-C, D-D, D-E.

Figure 6:
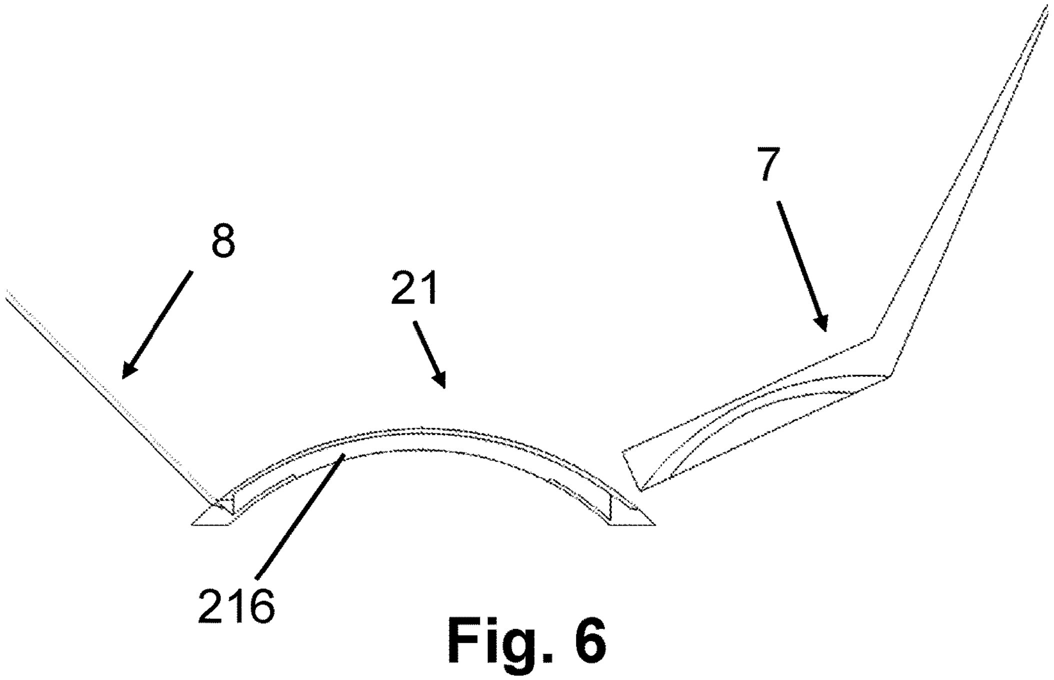
FIG. 6 illustrates a configuration for the insertion of a cornea implant into a patient cornea in accordance with the present disclosure in a schematic side view.
Figure 7:
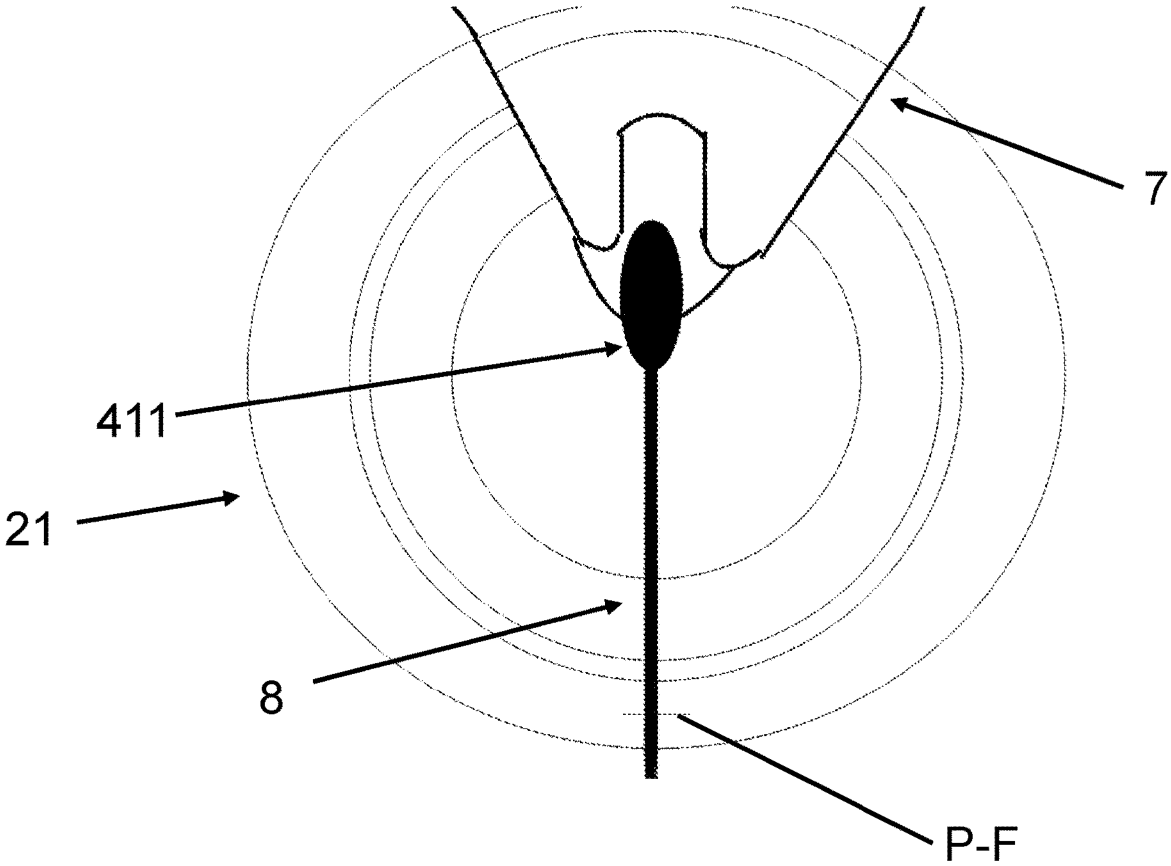
FIG. 7 illustrates the positioning of a cornea implant in accordance with the present disclosure in a schematic top view.

In the following, reference is additionally made to FIG. 6 and FIG. 7, schematically illustrating the insertion and placing of the cornea implant 411 in the patient cornea 21. FIG. 6 illustrated the situation prior the actual insertion if the cornea implant 411. An insertion spatula 7 with the cornea implant 411 (not visible in FIG. 6) is positioned to allow introduction via the patient access cut P-E (not visible in FIGS. 6 and 7) into the patient cornea cavity 216 which has been created before by resecting and removing the patient cornea tissue element 211 as mentioned. Further, auxiliary forceps are positioned and introduced into the patient cornea cavity 416 via the auxiliary patient access cut P-F.

FIG. 7 illustrates the positioning of the cornea implant 411 in a schematic top view. By grasping the cornea implant 411 with auxiliary forceps 8, the cornea implant 8 can maneuvered, in particular pulled, into the correct position within the patient cornea cavity 216. In the schematic illustration of FIG. 7, the cornea implant 411 is directly grasped in a peripheral region by auxiliary forceps 8. It may, however, also be manipulated differently, for example via a length of suture which is fixed to the cornea implant 411 in its peripheral region.

REFERENCE SIGNS

1 ophthalmological treatment and manufacture apparatus control device/control device
1' functional unit
15 general-purpose computing device
16 input unit
17 output unit
171 image area
2 patient eye
21 patient cornea
21' patient cornea tissue ring
21*a* patient anterior cornea surface
21*p* patient posterior cornea surface
211 patient cornea element
211*a* patient anterior cornea element surface
211*p* patient posterior cornea element surface
212 circumferential edge of patient anterior lamellar cut/anterior edge of patient side cut
213 circumferential outer edge of patient posterior lamellar cut/posterior edge of patient side cut
214 circumferential inner edge of patient posterior lamellar cut/anterior edge of patient auxiliary side cut
216 patient cornea cavity
22 lens
23 retina
29 sclera
3 ophthalmological laser device/laser device
31 patient interface
32 radiation cone
33 suction ring
41 donor cornea
41' donor cornea tissue ring
41*a* donor anterior cornea surface
41*p* donor posterior cornea surface
411 cornea implant
411*a* cornea implant anterior surface
411*p* cornea implant posterior surface
412 circumferential edge of donor anterior lamella cut; posterior edge of patient access cut
413 circumferential outer edge of donor posterior lamellar cut/posterior edge of donor side cut
414 circumferential inner edge of donor posterior lamellar cut/anterior edge of auxiliary side cut
415 anterior edge of donor side cut
5 cornea implant
5*a* cornea implant anterior surface
5*p* cornea implant posterior surface
6 donor cover element
7 insertion spatula
8 auxiliary forceps
a anterior-point direction
p posterior-pointing direction
i inwards-pointing direction
outwards-pointing direction
r radius of patient cornea element
r' radius of cornea implant
CIA corneal implant axis
PCA patient cornea axis
DCA donor cornea axis
P-A patient auxiliary side cut
P-B patient posterior lamellar cut
P-C patient side cut
P-D patient anterior lamellar cut
P-E patient access cut
P-F auxiliary patient access cut
D-A donor auxiliary side cut.
D-B donor posterior lamellar cut
D-C donor side cut
D-D donor anterior lamellar cut
D-E donor access cut

The invention claimed is:

1. Ophthalmological treatment apparatus for resecting a patient cornea element form a patient cornea in posterior lamellar keratoplasty, the ophthalmological treatment apparatus including:

a) a treatment laser device for implementing cornea cuts;

b) a computerized treatment control device in operative coupling with the treatment laser device, the treatment control device configured to control the treatment laser device to implement a number of patient cornea cuts, the patient cornea cuts forming, in combination, a patient cornea cut pattern with a geometry of the patient cornea element being defined by the patient cornea cut pattern, the number of patient cornea cuts including:

a patient anterior lamellar cut, the patient anterior lamellar cut extending in the patient cornea at a patient anterior lamellar cut distance from a patient posterior cornea surface of the patient cornea, the patient anterior lamellar cut defining a patient anterior cornea element surface, a patient side cut, the patient side cut extending in the patient cornea from a circumferential edge of the patient anterior lamellar cut towards the patient posterior cornea surface in a circumferentially closed manner, the patient side cut defining, at least in part, a circumferential patient cornea element surface, a patient access cut, the patient access cut extending in the patient cornea from the patient side cut to a peripheral region of the patient anterior cornea surface, the patient access cut forming an access passage in the patient cornea, the patient cornea cut pattern further defining a patient cornea interlocking structure, the patient cornea interlocking structure being configured to interlock the patient cornea with a cornea implant after replacing the patient cornea element by the cornea implant, wherein the patient cornea cut pattern includes an auxiliary patient access cut, the auxiliary patient access cut extending in the patient cornea from the patient side cut to the peripheral region of the patient anterior cornea surface, wherein the auxiliary patient access cut is arranged with respect to a circumference of the patient side cut opposite to the patient access cut, the auxiliary patient access cut forming an auxiliary access passage in the patient cornea.

2. Ophthalmological treatment apparatus according to claim 1, wherein the treatment control device is configured to control the treatment laser device to implement the patient anterior lamellar cut subsequent to the patient side cut and the patient access cut subsequent to the patient anterior lamellar cut.

3. Ophthalmological treatment apparatus according to claim 1, wherein the patient side cut does not extend to the patient posterior cornea surface, the patient cornea cut pattern further including:

a patient posterior lamellar cut, the patient posterior lamellar cut extending circumferentially in the patient cornea from a posterior edge of the patient side cut inwards with respect to the patient cornea, in particular with a constant distance to the patient anterior lamellar cut, a patient auxiliary side cut, the patient auxiliary side cut extending from an inner edge of the patient posterior lamellar cut to the patient posterior cornea surface.

4. Ophthalmological treatment apparatus according to claim 3, wherein the treatment control device is configured to control the treatment laser device to implement the patient posterior lamellar cut subsequent to the patient auxiliary side cut and prior to the patient side cut.

5. Ophthalmological treatment apparatus according to claim 1, wherein the patient cornea interlocking structure is defined, at least in part, by a patient posterior cornea element surface.

6. Ophthalmological treatment apparatus according to claim 1, wherein the patient cornea element includes a circumferential step in a peripheral region of a patient posterior cornea.

7. Ophthalmological treatment apparatus according to claim 1, wherein the patient access cut meets the patient anterior cornea surface in an acute angle.

8. Ophthalmological treatment apparatus according to claim 1, wherein the patient auxiliary access cut meets the patient anterior cornea surface in a perpendicular manner.

9. Ophthalmological treatment apparatus according to claim 1, wherein the treatment control device is configured to implement the patient cornea cuts that define the geometry of the patient cornea element in sequence one after the other.

* * * * *